(12) United States Patent
Cooper et al.

(10) Patent No.: US 6,451,027 B1
(45) Date of Patent: Sep. 17, 2002

(54) DEVICES AND METHODS FOR MOVING AN IMAGE CAPTURE DEVICE IN TELESURGICAL SYSTEMS

(75) Inventors: Thomas G. Cooper, Menlo Park; Dean F. Hoornaert, Mountain View; Steven J. Blumenkranz, Redwood City, all of CA (US)

(73) Assignee: Intuitive Surgical, Inc., Mountain View, CA (US)

( * ) Notice: Subject to any disclaimer, the term of this patent is extended or adjusted under 35 U.S.C. 154(b) by 0 days.

(21) Appl. No.: 09/464,287

(22) Filed: Dec. 15, 1999

Related U.S. Application Data

(60) Provisional application No. 60/112,990, filed on Dec. 16, 1998.

(51) Int. Cl.$^7$ ............................................. A61B 19/00

(52) U.S. Cl. ............................ 606/130; 901/19; 901/27

(58) Field of Search ........................ 600/102; 606/130; 901/27, 28, 19

(56) References Cited

U.S. PATENT DOCUMENTS

| | | |
|---|---|---|
| 4,437,635 A | 3/1984 | Pham |
| 4,975,016 A | 12/1990 | Pellenc et al. |
| 5,222,409 A | 6/1993 | Dalakian |
| 5,397,323 A | 3/1995 | Taylor et al. |
| 5,502,363 A | 3/1996 | Tasch et al. |
| 5,695,500 A | 12/1997 | Taylor et al. |
| 5,762,458 A | 6/1998 | Weang et al. |
| 5,800,423 A | 9/1998 | Jensen |
| 5,808,665 A | 9/1998 | Green |
| 5,817,084 A | 10/1998 | Jensen |
| 5,876,325 A | 3/1999 | Mizuno et al. |
| 5,888,190 A * | 3/1999 | Meyer et al. ............... 600/102 |

OTHER PUBLICATIONS

Asada et al., "Development of a direct–drive arm using high torque brushless motors" Robotics Research, Brady et al., Eds. (1984) MIT Press, Chapter 7, pp. 583–599.

Fayet et al., "Polyarticulated mechanical structure for robot decoupling the positioning and orientation" Symposium on Theory and Practice of Robots and Manipulators Sep. 9–12, 1986, Poland, pp. 386–494.

Hunter et al., "A teleoperated microsurgical robot and associated virtual environment for eye surgery" Presence: Teleoperators and Virtual Environments (1994) 2(4):MIT Press, pp. 265–280.

Hurteau et al., "Laparoscopic surgery assisted by a robotic cameraman: Concept and experimental results" Proceeding 1994 IEEE International Conference on Robotics and Automation, May 8–13, 1994, pp. 2286–2289.

(List continued on next page.)

*Primary Examiner*—Linda C. M. Dvorak
*Assistant Examiner*—Jocelyn Ram
(74) *Attorney, Agent, or Firm*—Townsend Townsend & Crew LLP; Mark D. Barrish, Esq.

(57) ABSTRACT

A positional control system, comprising a robotically controlled arm, for varying the position of a robotic surgical tool, is provided. The robotic surgical tool can be in the form of an image capture device, such as an endoscope, for example. The positional control system comprises a base and a mounting formation arranged to support the robotic surgical tool. The positional control system further comprises an articulated arm extending between the base and the mounting formation. The articulated arm has an upper arm portion, a forearm portion, a forearm link member and an upper arm link member. The portions and the link members are pivotally secured relative to one another to effect displacement of the mounting formation relative to the base. The forearm link member is positioned at least partially within the forearm portion and the upper arm link member is positioned at least partially within the upper arm portion.

8 Claims, 17 Drawing Sheets

OTHER PUBLICATIONS

Kazerooni, "Design and analysis of the statically balanced direct–drive robot manipulator" Robotics & Computer–Integrated Manufacturing (1989) 6(4):287–293.

Lawson et al., "Linear least squares with linear inequality constraints" Solving Least Squares Problems Prentice Hall, Inc. (1974) pp. 158–173.

Madhani et al., "The black falcon: A teleoperated surgical instrument for minimally invasive surgery" (submitted to IROS (1998) 9 pages total.

Moyer, "The design for an integrated hand and wrist mechanism" Masters Thesis, Massachusetts Institute of Technology, (Feb. 1992) pp. 1–106.

"Task 2: Miniature end effector—A preliminary design" pp. 32–47.

Taylor et al., "A telerobotic assistant for laparoscopic surgery" IEEE Engineering in Medicine and Biology (1995) pp. 279–288.

Yan et al., "Design and control of a motion scaling system for microsurgery experiments" Department of Electrical Engineering, University of British Columbia, pp. 211–216.

Handbook of Industrial Robotics. Ed. Shimon Y. Nof. 1985. p. 36–7.*

* cited by examiner

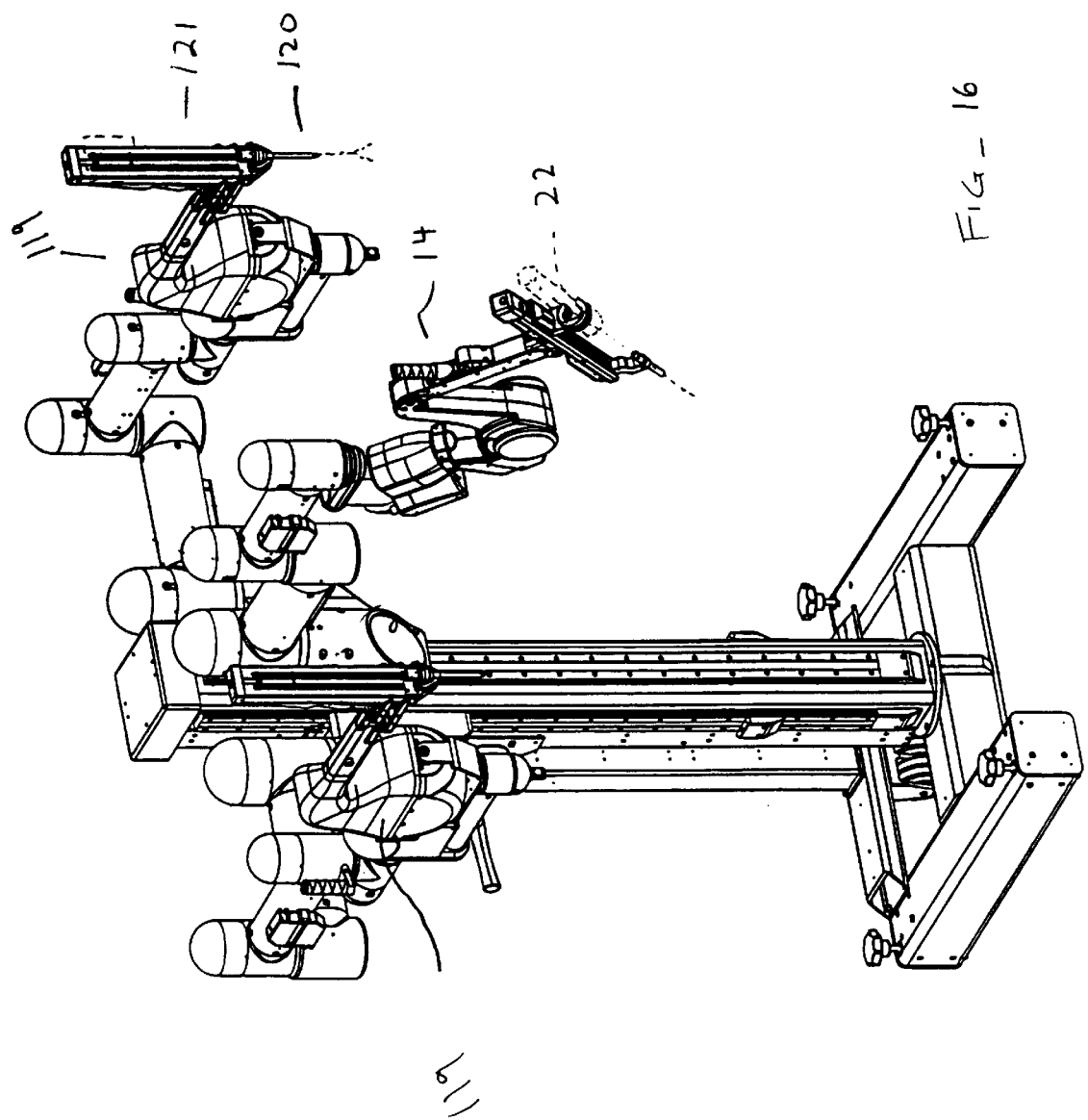

DEVICES AND METHODS FOR MOVING AN IMAGE CAPTURE DEVICE IN TELESURGICAL SYSTEMS

RELATED APPLICATIONS

This application claims priority from U.S. Provisional Patent Application No. 60/112,990, filed Dec. 16, 1998. Furthermore, this application is related to co-pending U.S. patent application Ser. No. 09/475,406, entitled "Image Shifting Apparatus and Method for a Telerobotic System," filed Dec. 7, 1999 and co-pending U.S. patent application Ser. No. 09/464,455, entitled "Devices and Methods for Presenting and Regulating Auxiliary Information on an Image Display of a Telesurgical System to Assist an Operator in Performing a Surgical Procedure," filed Dec. 14, 1999, the full disclosures of which are incorporated herein by reference. This application is also related to the following patents and patent applications, the full disclosures of which are incorporated herein by reference: PCT International Application No. PCT/US98/19508, entitled "Robotic Apparatus," filed on Sep. 18, 1998; U.S. patent application Ser. No. 09/418,726, entitled "Surgical Robotic Tools, Data Architecture, and Use," filed on Oct. 15, 1999; U.S. patent application Ser. No. 09/378,173, entitled "Stereo Imaging System for Use in Telerobotic Systems," filed on Aug. 20, 1999; U.S. patent application Ser. No. 09/398,507, entitled "Master Having Redundant Degrees of Freedom," filed Sep. 17, 1999; U.S. patent application Ser. No. 09/288,068, entitled "Aspects of a Control System of a Minimally Invasive Surgical Apparatus;" filed Apr. 7, 1999; U.S. patent application Ser. No. 09/373,678, entitled "Camera Referenced Control in a Minimally Invasive Surgical Apparatus," filed Aug. 13, 1999; U.S. patent application Ser. No. 09/398,960, entitled "Repositioning and Orientation of Master/Slave Relationship in Minimally Invasive Telesurgery," filed Sep. 17, 1999; and U.S. Pat. No. 5,808,665, entitled "Endoscopic Surgical Instrument and Method for Use," issued on Sep. 15, 1998.

BACKGROUND OF THE INVENTION

The present invention is generally related to improved robotic devices, systems and methods, for use in telerobotic surgery.

Minimally invasive medical techniques are aimed at reducing the amount of extraneous tissue which may be damaged during diagnostic or surgical procedures, thereby reducing patient recovery time, discomfort, and deleterious side effects. Many surgeries are performed each year in the United States. A significant amount of these surgeries can potentially be performed in a minimally invasive manner. However, only a relatively small percentage of surgeries currently use minimally invasive techniques due to limitations of minimally invasive surgical instruments and techniques currently used and the difficulty experienced in performing surgeries using such traditional instruments and techniques.

Advances in minimally invasive surgical technology could dramatically increase the number of surgeries performed in a minimally invasive manner. The average length of a hospital stay for a standard surgery is significantly longer than the average length for the equivalent surgery performed in a minimally invasive surgical manner. Thus, expansion in the use of minimally invasive techniques could save millions of hospital days, and consequently millions of dollars annually, in hospital residency costs alone. Patient recovery times, patient discomfort, surgical side effects, and time away from work can also be reduced by expanding the use of minimally invasive surgery.

Traditional forms of minimally invasive surgery include endoscopy. One of the more common forms of endoscopy is laparoscopy, which is minimally invasive inspection or surgery within the abdominal cavity. In traditional laparoscopic surgery a patient's abdominal cavity is insufflated with gas and cannula sleeves are passed through small (approximately ½ inch) incisions in the musculature of the patient's abdomen to provide entry ports through which laparoscopic surgical instruments can be passed in a sealed fashion.

The laparoscopic surgical instruments generally include a laparoscope for viewing the surgical field and working tools defining end effectors. Typical surgical end effectors include clamps, graspers, scissors, staplers, and needle holders, for example. The working tools are similar to those used in conventional (open) surgery, except that the working end or end effector of each tool is separated from its handle by an approximately 12-inch long extension tube, for example, so as to permit the surgeon to introduce the end effector to the surgical site and to control movement of the end effector relative to the surgical site from outside a patient's body.

To perform surgical procedures, the surgeon typically passes these working tools or instruments through the cannula sleeves to the internal surgical site and manipulates the instruments or tools from outside the abdomen by sliding them in and out through the cannula sleeves, rotating them in the cannula sleeves, levering (i.e., pivoting) the instruments against the abdominal wall and actuating the end effectors on the distal ends of the instruments from outside the abdominal cavity. The instruments normally pivot around centers defined by the incisions which extend through the muscles of the abdominal wall. The surgeon typically monitors the procedure by means of a television monitor which displays an image of the surgical site via the laparoscopic camera. Typically, the laparoscopic camera is also introduced through the abdominal wall so as to capture an image of the surgical site. Similar endoscopic techniques are employed in, e.g., arthroscopy, retroperitoneoscopy, pelviscopy, nephroscopy, cystoscopy, cisternoscopy, sinoscopy, hysteroscopy, urethroscopy, and the like.

There are many disadvantages relating to such traditional minimally invasive surgical (MIS) techniques. For example, existing MIS instruments deny the surgeon the flexibility of tool placement found in open surgery. Difficulty is experienced in approaching the surgical site with the instruments through the small incisions. The length and construction of many endoscopic instruments reduces the surgeon's ability to feel forces exerted by tissues and organs on the end effector of the associated instrument. Furthermore, coordination of the movement of the end effector of the instrument as viewed in the image on the television monitor with actual end effector movement is particularly difficult, since the movement as perceived in the image normally does not correspond intuitively with the actual end effector movement. Accordingly, lack of intuitive response to surgical instrument movement input is often experienced. Such a lack of intuitiveness, dexterity and sensitivity of endoscopic tools has been found to be an impediment to the expansion of the use of minimally invasive surgery.

Minimally invasive telesurgical systems for use in surgery have been and are still being developed to increase a surgeon's dexterity as well as to permit a surgeon to operate on a patient in an intuitive manner. Telesurgery is a general term for surgical systems where the surgeon uses some form of remote control, e.g., a servomechanism, or the like, to manipulate surgical instrument movements, rather than directly holding and moving the tools by hand. In such a telesurgery system, the surgeon is typically provided with an image of the surgical site on a visual display at a location remote from the patient. The surgeon can typically perform the surgical procedure at the location remote from the patient whilst viewing the end effector movement during the surgical procedure on the visual display. While viewing typically a three-dimensional image of the surgical site on the visual display, the surgeon performs the surgical procedures on the patient by manipulating master control devices at the remote location, which master control devices control motion of the remotely controlled instruments.

Typically, such a telesurgery system can be provided with at least two master control devices (one for each of the surgeon's hands), which are normally operatively associated with two robotic arms on each of which a surgical instrument is mounted. Operative communication between master control devices and associated robotic arm and instrument assemblies is typically achieved through a control system. The control system typically includes at least one processor which relays input commands from the master control devices to the associated robotic arm and instrument assemblies and from the arm and instrument assemblies to the associated master control devices in the case of, e.g., force feedback, or the like.

It is an object of this invention to provide a suitable robotically controlled image capture system for capturing an image of a surgical site on which a surgical procedure is to be performed. It is another object of this invention to provide an image capture positional control system which can advantageously be used in minimally invasive surgical applications.

SUMMARY OF THE INVENTION

In accordance with one aspect of the invention, there is provided a positional control system for varying the position of a robotic surgical tool, such as an image capture device, for example, the positional control system comprising a base; a mounting formation arranged to support the robotic surgical tool; and an articulated arm extending between the base and the mounting formation, the articulated arm having an upper arm portion, a forearm portion, a forearm link member and an upper arm link member, the portions and link members being pivotally secured relative to one other to effect displacement of the mounting formation relative to the base, the forearm link member being positioned at least partially within the forearm portion and the upper arm link member being positioned at least partially within the upper arm portion.

In accordance with another aspect of the invention, there is provided a positional control system for varying the position of a robotic surgical tool, the positional control system comprising a base; an articulated arm having an end portion mounted on the base and an opposed end portion arranged to be positionally adjustable relative to the base; a mounting formation operatively connected to the opposed end portion of the articulated arm; and a mounting bracket releasably mountable on the mounting formation and arranged to hold a robotic surgical tool.

In accordance with yet another aspect of the invention, there is provided a positional control system for varying the position of a robotic surgical tool, the positional control system comprising a base; an articulated arm having an end portion mounted on the base and an opposed end portion arranged to be positionally adjustable relative to the base; a support on the opposed end portion of the arm; a mounting formation, on which the robotic surgical tool is mountable, mounted on the support; and a cannula mount quick releasably mountable on the support.

The cannula mount may include an engagement pin releasably lockable in a complementary locking mechanism on the support.

In accordance with a further aspect of the invention, there is provided a positional control system for varying the position of a robotic surgical tool, the positional control system comprising a base; an articulated arm having an end portion mounted on the base and an opposed end portion arranged to be positionally adjustable relative to the base; a mounting formation, on the opposed end portion of the articulated arm, arranged to support the robotic surgical tool; at least one actuator for driving the articulated arm to cause positional adjustment of the opposed end portion relative to the base; and at least one harmonic drive operatively positioned between the actuator and the articulated arm.

In accordance with yet another aspect of the invention, there is provided a positional control system for varying the position of a robotic surgical tool, the positional control system comprising a base; an articulated arm having an end portion mounted on the base and an opposed end portion arranged to be positionally adjustable relative to the base; and a robotic surgical tool support operatively connected to the opposed end portion of the arm, the support defining a seat for holding the robotic surgical tool and including an at least part circumferential track, the support being mounted on the opposed end portion of the arm by means of rollers cooperating with said track so as to permit angular displacement of the support relative to the opposed end of the arm.

In accordance with yet another aspect of the invention, there is provided a positional control system for varying the position of a robotic surgical tool, the positional control system including a base; an articulated arm having an end portion mounted on the base and an opposed end portion arranged to be positionally adjustable relative to the base; and a robotic surgical tool support, the support defining a seat for holding the robotic surgical tool and an opening leading to the seat to permit the robotic surgical tool to be passed laterally through the opening and then to be dropped into the seat.

In accordance with yet another aspect of the invention, there is provided a positional control system for varying the position of a robotic surgical tool, the positional control system including a base; an articulated arm having an end portion mounted on the base and an opposed end portion arranged to be positionally adjustable relative to the base; a mounting formation on the opposed end portion of the articulated arm and arranged to support the robotic surgical tool, the mounting formation being mounted relative to the opposed end of the arm to permit angular displacement relative thereto; and an actuator operatively connected to the mounting formation by means of an elongate element to transmit actuation of the actuator to the mounting formation through the elongate element.

BRIEF DESCRIPTION OF THE DRAWINGS

A preferred embodiment of the invention will now be described, by way of example, and with reference to the accompanying diagrammatic drawings, in which:

FIG. 16 is a perspective view of an exemplary cart structure with positioning linkages which support robotic manipulators.

DESCRIPTION OF THE SPECIFIC EMBODIMENTS

Figure 1:
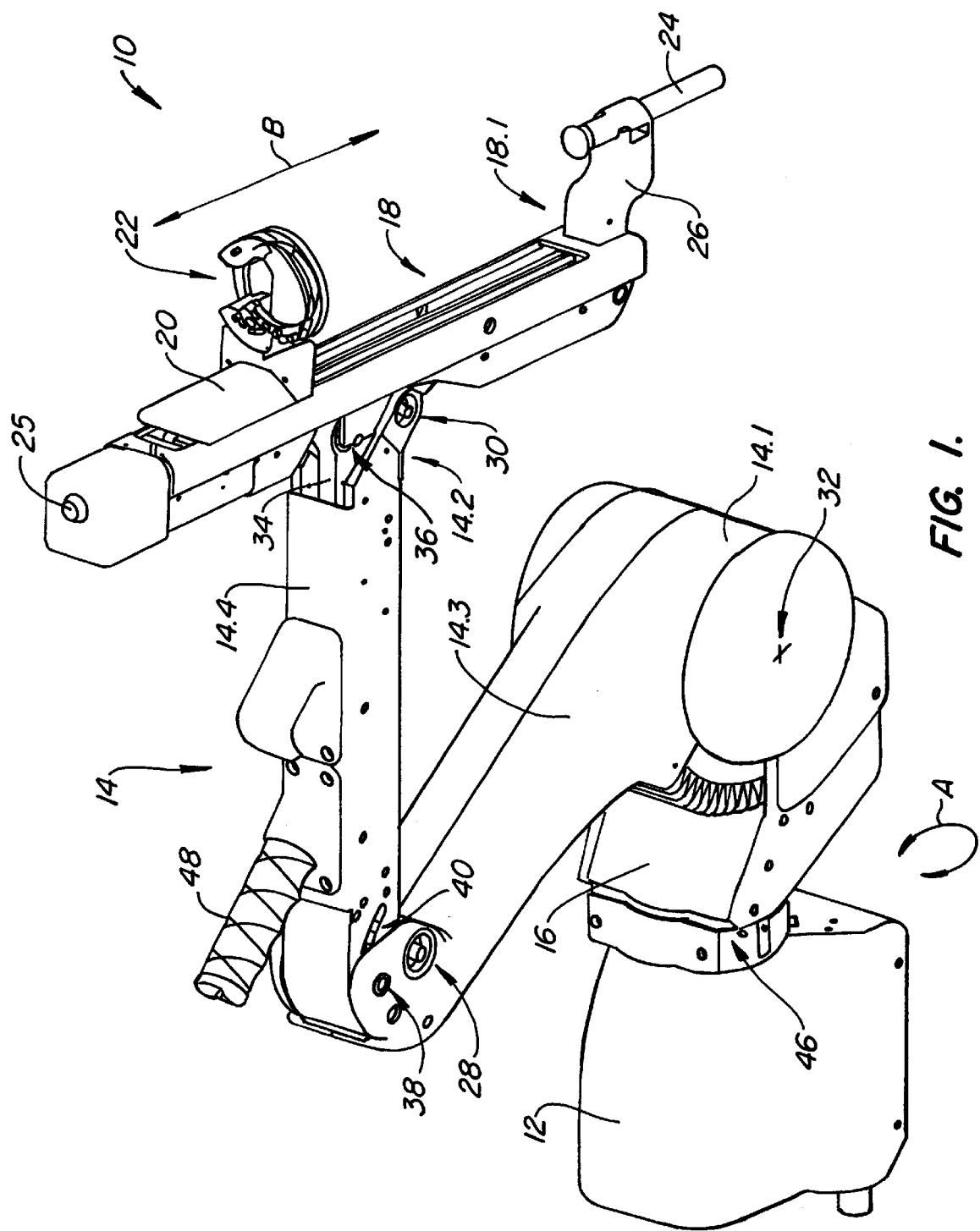
FIG. 1 shows a three-dimensional view of part of a positional control system, comprising a robotically controlled arm, for an image capture device, in accordance with the invention.
Figure 2:
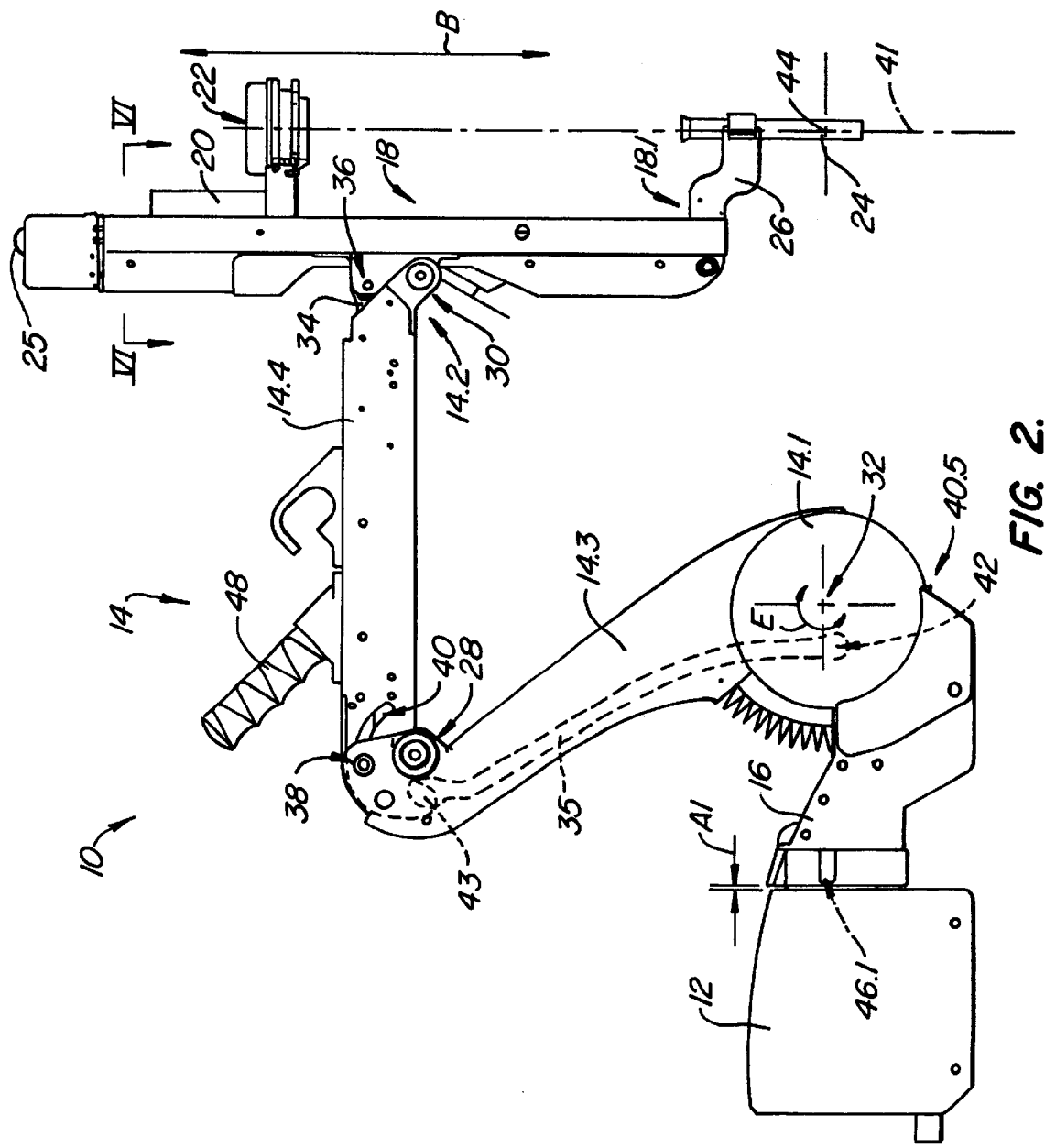
FIG. 2 shows a side elevation of the arm shown in FIG. 1.

Referring initially to FIGS. 1 and 2 of the drawings, part of a positional control system for an image capture device e.g. an endoscope, in accordance with the invention, is generally indicated by reference numeral 10.

It will be appreciated that the rest of the positional control system includes a remotely positioned master control device or devices (not shown) whereby the part of the system 10 can be caused to displace in response to manipulation of the master control device or devices at a remote location. This can typically be achieved by means of actuators, e.g., servo motors, in operative communication with the master control device or devices and the part of the positional control system 10. Refer to co-pending U.S. patent application Ser. No. 09/475,406, entitled "Image Shifting Apparatus and Method for a Telerobotic System," filed Dec. 7, 1999, the full disclosure of which is incorporated herein by reference, for further details in connection with displacement of the part of the system 10 in response to manipulation of the master control device or devices at a remote location.

The part of the system 10 includes a base 12. It further includes an articulated arm, generally indicated by reference numeral 14. The arm 14 has one end portion 14.1 mounted on a cradle 16. The cradle 16 is mounted on the base 12 gimbaled fashion. Thus, it is capable of angular displacement, or yaw, relative to the base 12 as indicated by arrows A in FIG. 1. The cradle 16 is angularly displaceable in the direction of arrows A in FIG. 1 about a single shaft by which the cradle 16 is rotatably mounted on the base 12. The shaft is indicated at 46 and defines a rotational axis 46.1 as can best be seen in FIGS. 2 and 3. The cradle 16 is typically driven by an appropriate actuator, e.g., an electric motor, or the like, to yaw about the axis 46.1 as indicated by the arrows A. Thus, the connection of the cradle 16 to the base 12 is in the form of a cantilevered yaw drive.

A guide formation or support, generally indicated by reference numeral 18, is connected to an opposed end 14.2 of the arm 14. A carriage 20 is mounted on the guide formation 18. The guide formation 18 defines a linear path as represented by arrows B. The carriage 20 is arranged to be displaceable along the linear path defined by the guide formation 18 in the directions indicated by arrows B. An image capture device mounting formation, in this case an endoscope mounting formation, is indicated by reference numeral 22. A cannula mount, on which a cannula 24 is quick releasably mountable, is indicated by reference numeral 26. The cannula mount 26 is quick releasably securable to an end portion 18.1 of the guide formation 18.

The articulated arm 14 includes an upper arm portion 14.3 and a forearm portion 14.4.

The upper and forearm portions 14.3, 14.4 are pivotally connected together at 28. Furthermore, the forearm portion 14.4 is pivotally connected to the guide formation 18 at 30 and the upper arm portion 14.3 is pivotally connected to the cradle 16 at 32. The upper and forearm portions 14.3, 14.4 are in the form of hollow box-sections. A forearm elongate link member 34 is positioned within the forearm portion 14.4. One end of the link member 34 is pivotally connected to the guide formation 18 at 36, and an opposed end is pivotally connected to the upper arm portion 14.3 at 38. A part-circular slot 40 extends through the forearm portion 14.4 at a predetermined radius from a center defined by a pivotal axis of the pivotal connection 28 so as to permit the pivotal connection 28 to pass from the link member 34 to the upper arm portion 14.3 through the forearm portion 14.4. As can be seen in FIG. 2, an upper arm elongate link member 35 is positioned within the upper arm portion 14.3. The upper arm elongate link member has one end pivotally connected to the cradle 16 at 42 and has an opposed end pivotally connected to the forearm portion 14.4 at 43. An advantage of providing the link 34 within the portion 14.4 and the link 35 within the portion 14.3 is that the potential of a person being pinched by the arm 14 is at least inhibited. The links and the portions often move laterally relative to each other in response to movement of the arm, especially pitching of the arm, and it can give rise to a person becoming pinched between the links and portions. By providing the links within the portions this risk is at least inhibited.

This type of construction—two pivotally-connected sets of parallel force-transmitting elements, each set comprising an elongate rod housed inside a hollow, parallel arm portion—allows a remote center of motion to be established without requiring the type of externally-obvious parallelogram arrangement typically necessary to establish a remote center of motion, such as is disclosed in U.S. Pat. No. 5,397,323. Instead, by arranging each set of parallel links by nesting one inside the other, the parallelogram relationship is maintained while minimizing the number of pinch points of concern and while also presenting a much simpler and cleaner profile to the surgical work environment. This simpler profile also occupies less room to operate over the surgical table and the patient, thereby minimizing possible collisions with other surgical equipment or other robotic surgical arms.

Figure 2A:
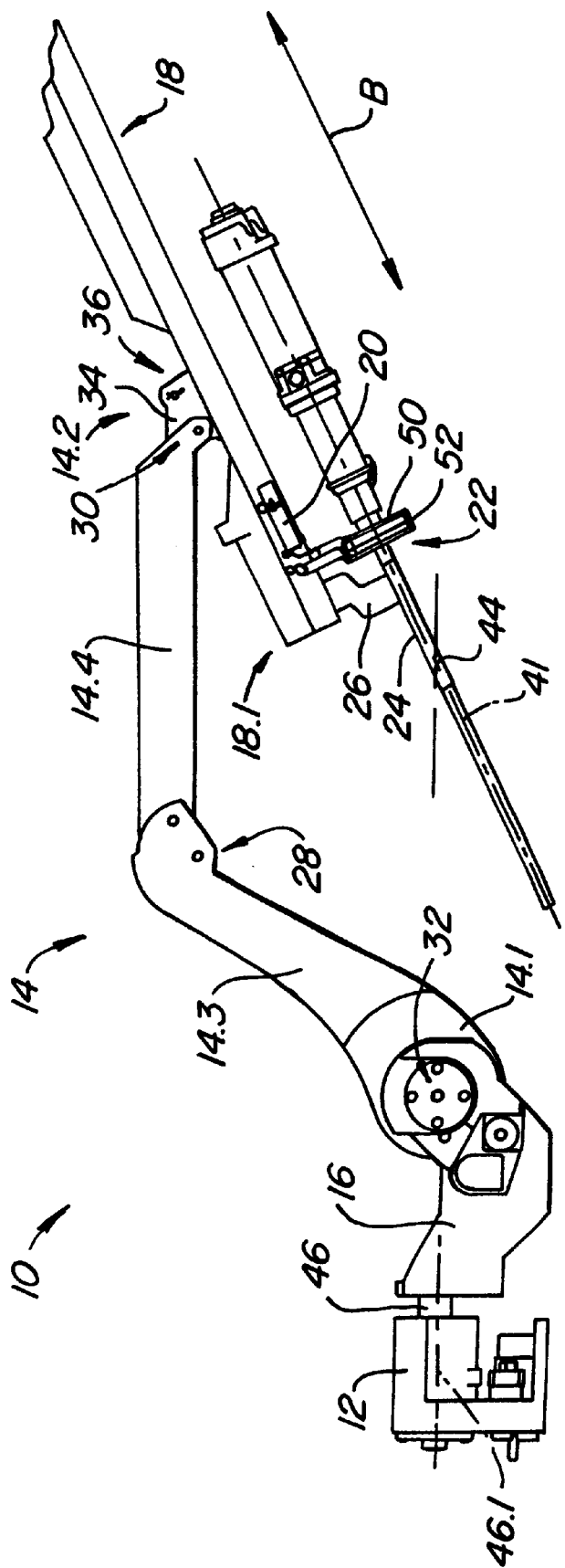
FIG. 2A shows, at a diminished scale, a side elevation corresponding to FIG. 2, the arm having been moved into another position.

Referring to FIGS. 2 and 2A, it will be seen that the arm portion 14.3 can pitch, or angularly displace about the pivotal connection 32, as indicated by arrows E. This is effected by an electrical motor (not shown) which engages teeth (not shown) defined on the upper arm portion 14.3. The electrical motor is typically a Maxon RE 035 motor with 1000 Pulse Per Revolution optical encoders with a gear ratio of 240:1 between the motor and the arm portion 14.3. The gear ratio of 240:1 is typically achieved by a direct 3:1 gear train and a harmonic drive with an 80:1 ratio. The harmonic drive is typically a harmonic drive which is available from Harmonic Drive Technologies™ having a part number HDL 20. The inclusion of the harmonic drive forms an important aspect of the invention since it provides, relative to other reduction systems, a high gear reduction in a compact form. It also provides for back drivability of the arm 14.

A harmonic drive in this robotic arm assembly provides a large ration of motor speed and torque, thus enabling a smaller motor to handle much larger loads than would otherwise be possible in the small space available for the gearing. Larger loads are experienced by the arm of the invention because of the weight of the endoscope and camera head that typically are manipulated by the arm. Furthermore, backdrivability is an important characteristic to the present invention because the surgeon's assistant, during a surgical procedure, may need to manually manipulate the endoscope in order to image certain portions of the surgical site for the surgeon to see. Without the ability to backdrive the drive motors and actuators, the assistant would essentially be unable to provide this service without either breaking the drive mechanism or having to physically disconnect the drive mechanism from the arm assembly.

Upon such angular displacement about 32 an axis 41 defined by the endoscope mounting formation 22 and the cannula mount 26 is caused to pivot about a remote pivot center indicated at 44 in FIG. 2A. During movement of the arm, the general position of the pivot center 44 does not change relative to the base 12. The pivot center 44, in use, is arranged to coincide with a port, e.g., an incision, natural aperture, or the like, in a patient body, through which port the endoscope is introduced such that a viewing or operative end of the endoscope can be positioned relative to a surgical site in the body so that an image of the surgical site can be displayed on a remote display screen or viewer. Upon movement of the arm, to change the position of the endoscope relative to the surgical site, in use, the pivot center 44 does not excessively move relative to the port of entry thus inhibiting damage to tissue surrounding the port of entry.

The cradle 16 is connected to the base 12 by the shaft 46 to permit angular displacement of the cradle 16 relative to the base 12 as indicated by the arrows A in FIG. 1. This is effected by an electrical motor similar to the one working on the upper arm portion 14.3. A reduction of 240:1 between the motor and the cradle 16 is typically also achieved by means of a 3:1 reduction gear and an 80:1 harmonic drive. It will be appreciated that a harmonic drive is included to provide back drivability of the arm 14. An advantage of cantilevering the cradle relative to the base as indicated, is to inhibit pinch points between the cradle and the base as they move relative to each other, in use. Accordingly, clearance between the cradle 16 and the base 12, as indicated at A1 in FIG. 1, is relatively small.

A further advantage of this cantilevered construction is to enable the entire robotic arm assembly to be supported at a single pivotal connection at the distal end of pivotable shaft 46, rather than also at a position, e.g., in the vicinity of 40.5 as shown in FIG. 2. Supporting a robotic surgical arm assembly in this manner allows the surgeon to position the arm assembly closer to the operating table and the patient with undue interference from an arm support structure on the side of the arm closest to the patient, which the present invention lacks.

It will be appreciated that, typically, when the part of the system 10 is used, a cannula is slipped onto an endoscope, and the endoscope is positioned at a general position relative to a surgical site on which it is desired to perform a surgical procedure. Once the cannula and endoscope are so positioned, the mounting formation 22 and the cannula mount 26 are brought to the endoscope and cannula, and the cannula and endoscope are then secured to the mount 26 and formation 22, respectively. Thus, back drivability, or movement of the articulated arm 14 independently of the motors is important to allow this to happen with relative ease.

It will be appreciated that the axis 41 pivots about the center 44 also when the cradle 16 is angularly displaced relative to the base 12 in a yaw fashion. Thus, the pivot center 44 is aligned with the axis of rotation of the cradle 16 relative to the base 12 at 46. 1, and the axis about which the upper arm portion 14.3 pivots relative to the cradle 16 at 32.

A handle 48 is provided to enable the articulated arm 14 to be brought into a general initial position when the endoscope is inserted through the port so as to align the remote center 44 with the port of entry, or incision, in the patient body. The endoscope can then be brought to a desired location by manipulation of the master controls, or by pushing clutch buttons 25 to release brakes to enable the floating of the arm and backdriveability of the arm.

Advantageously, the arm 14 is provided with brakes arranged automatically to brake the arm in its position and orientation in the event of a loss of power to the arm 14, for example. The arm is then retained in its position within its four degrees of freedom, namely, between the cradle and the base, the guide formation and the cradle, the carriage and the guide formation and the endoscope mounting formation and the carriage. The brakes typically cooperate with pivots at 32 and 46 to brake the arm. The brakes function as auto locks in the event of a loss of power, or the like. The clutch button 25 is arranged to release these brakes to permit floating of the arm when desired, for example, when coupling the arm to the endoscope as described above.

Figure 3:
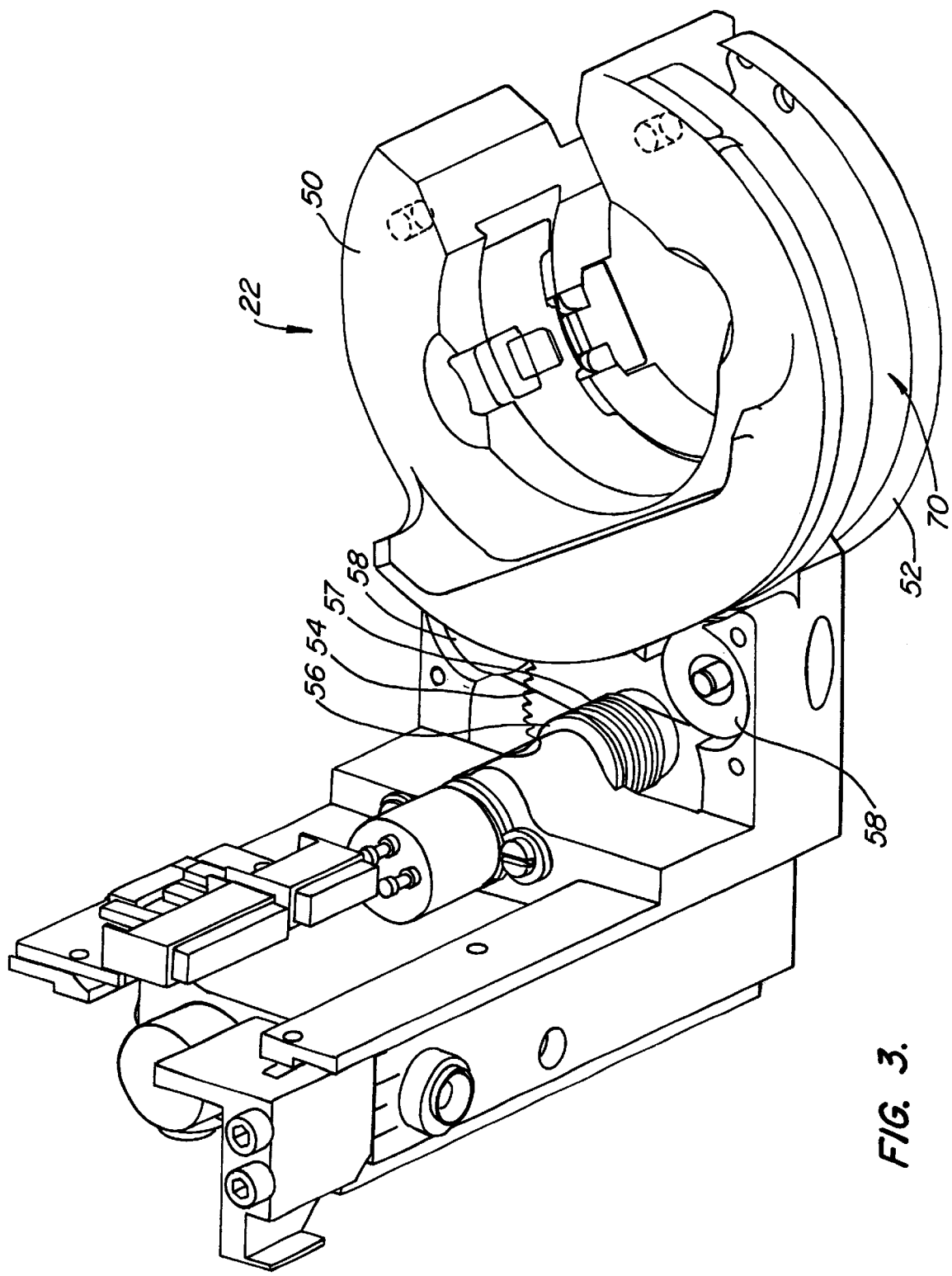
FIG. 3 shows a three-dimensional view of a mounting formation on the arm, on which mounting formation an endoscope is mountable.
Figure 4:
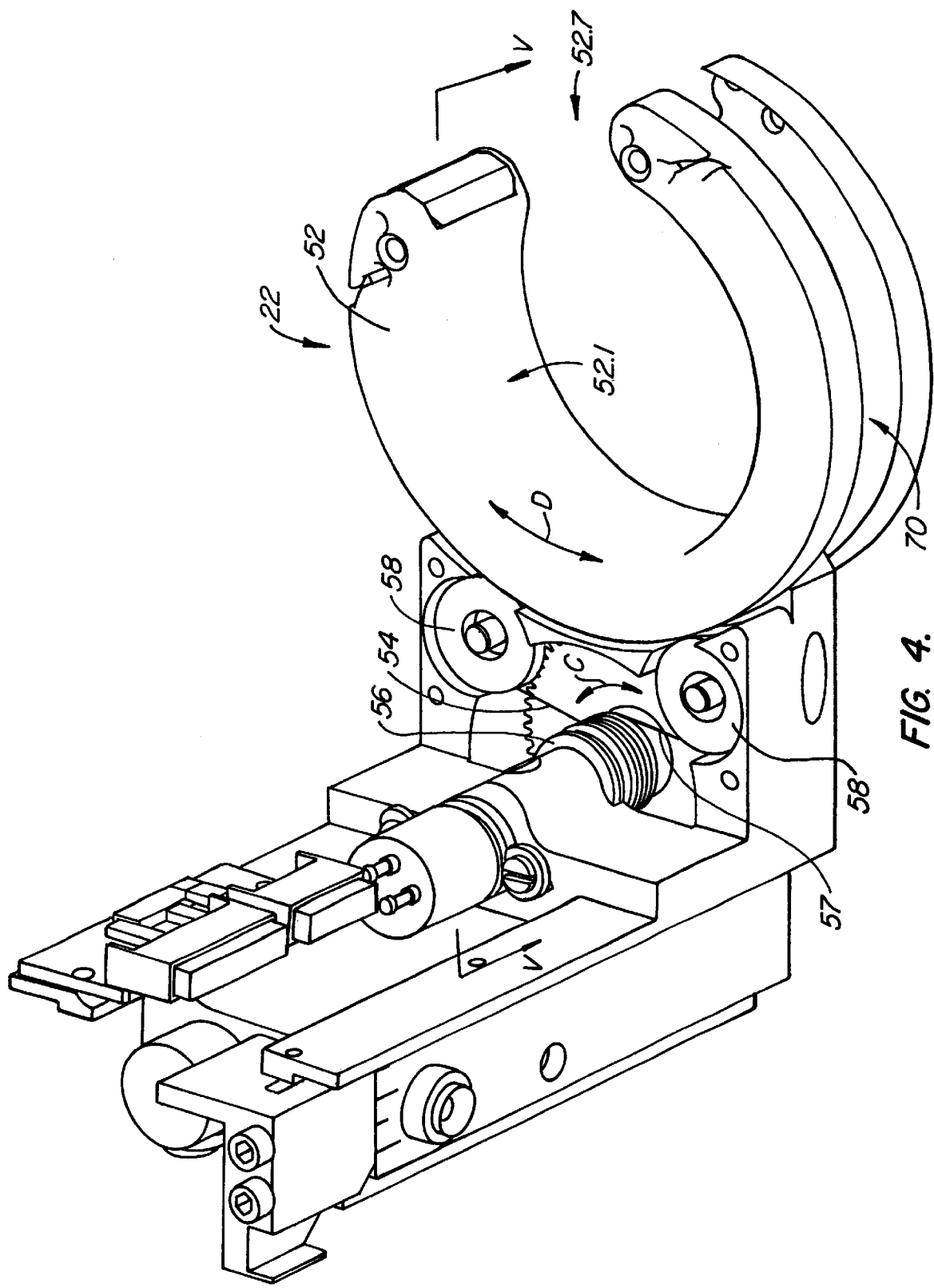
FIG. 4 is a three-dimensional view corresponding to FIG. 3, an endoscope mounting bracket having been removed from the mounting formation.
Figure 5:
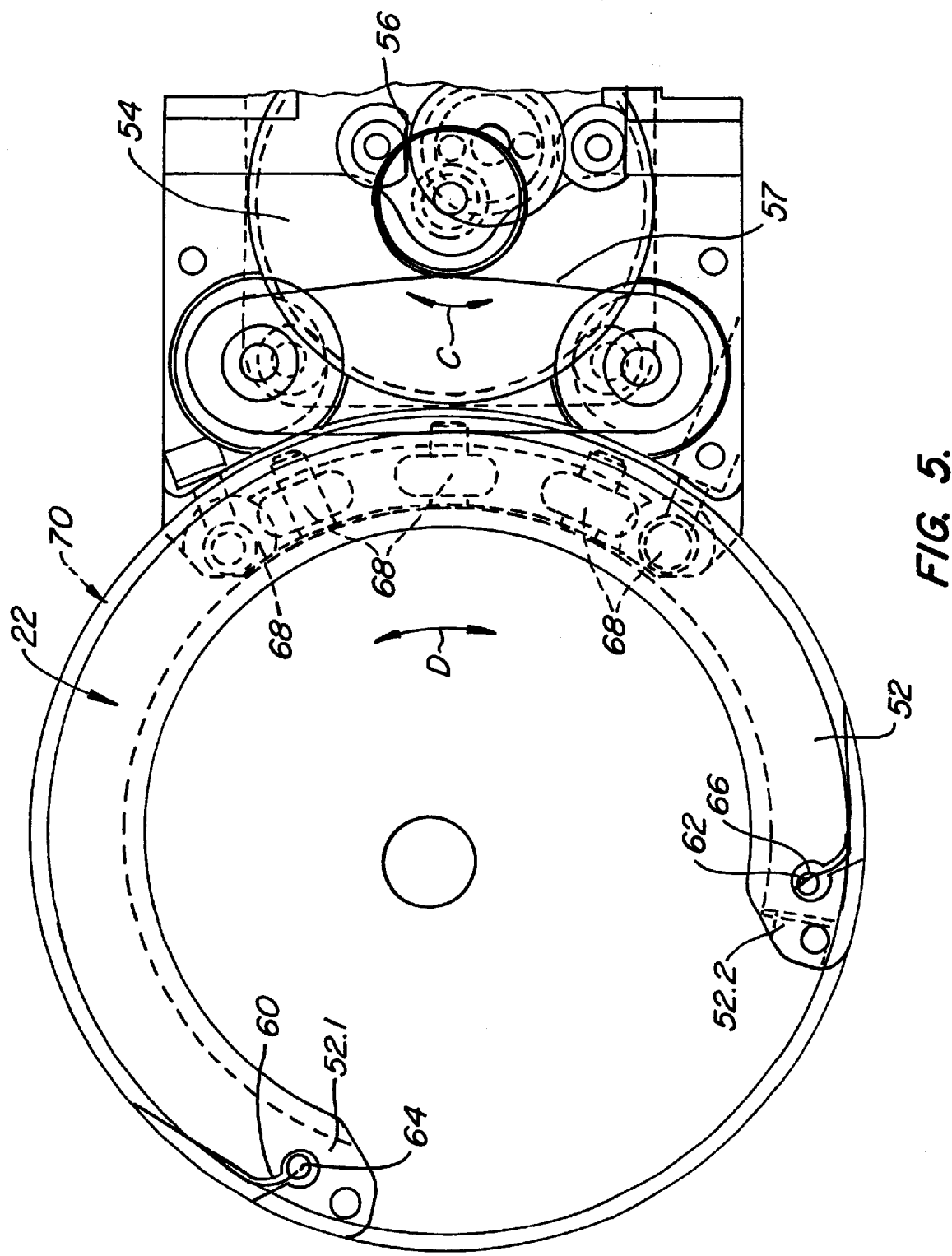
FIG. 5 shows, at an enlarged scale, a top view of a carriage and the mounting formation of FIG. 4, along arrows V—V in FIG. 4.

Referring to FIGS. 3 to 5, the endoscope mounting formation 22 includes a part annular collar or endoscope mounting bracket 50. The collar 50 is not shown in FIGS. 4 and 5 for the sake of clarity. The mounting formation 22 further comprises a part annular driven support 52. The collar 50 is removably mountable on the support 52 to provide an interface between the endoscope and the support 52. Accordingly, in use, and by means of the collar 50, a surgical drape can be used to cloak the part of the system 10 from a sterile surgical environment, the collar 50 then being used to mount the endoscope on the cloaked driven support 52 nesting fashion. The collar 50 and the support 52 have generally part circular apertures extending axially therethrough so as to locate an endoscope in the apertures. The collar 50 is typically sterilizable so that it can be sterilized between surgical operations performed using the arm 14.

Figure 9:
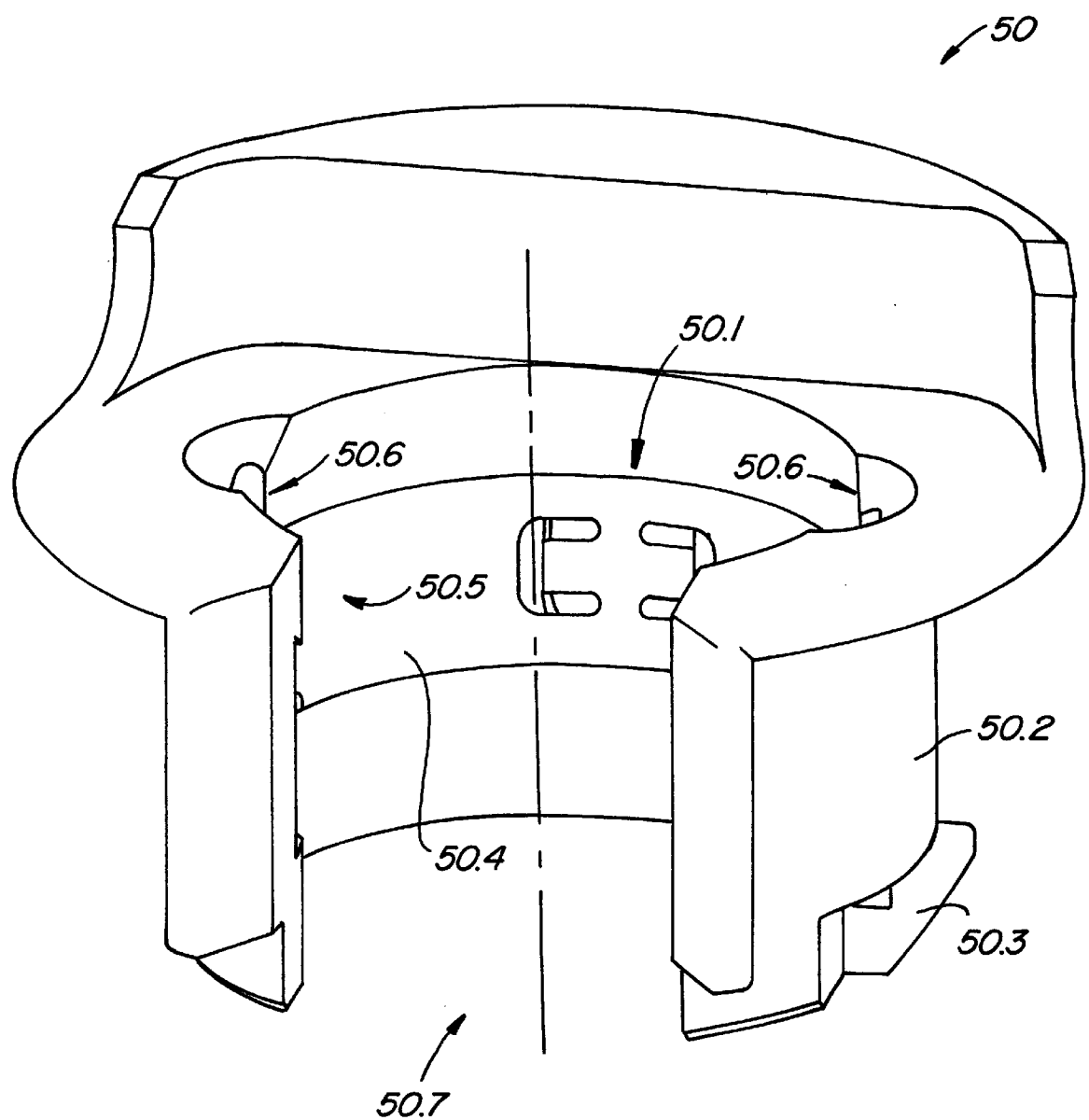
FIG. 9 shows a three-dimensional view of a collar for mounting an endoscope on the arm.
Figure 10:
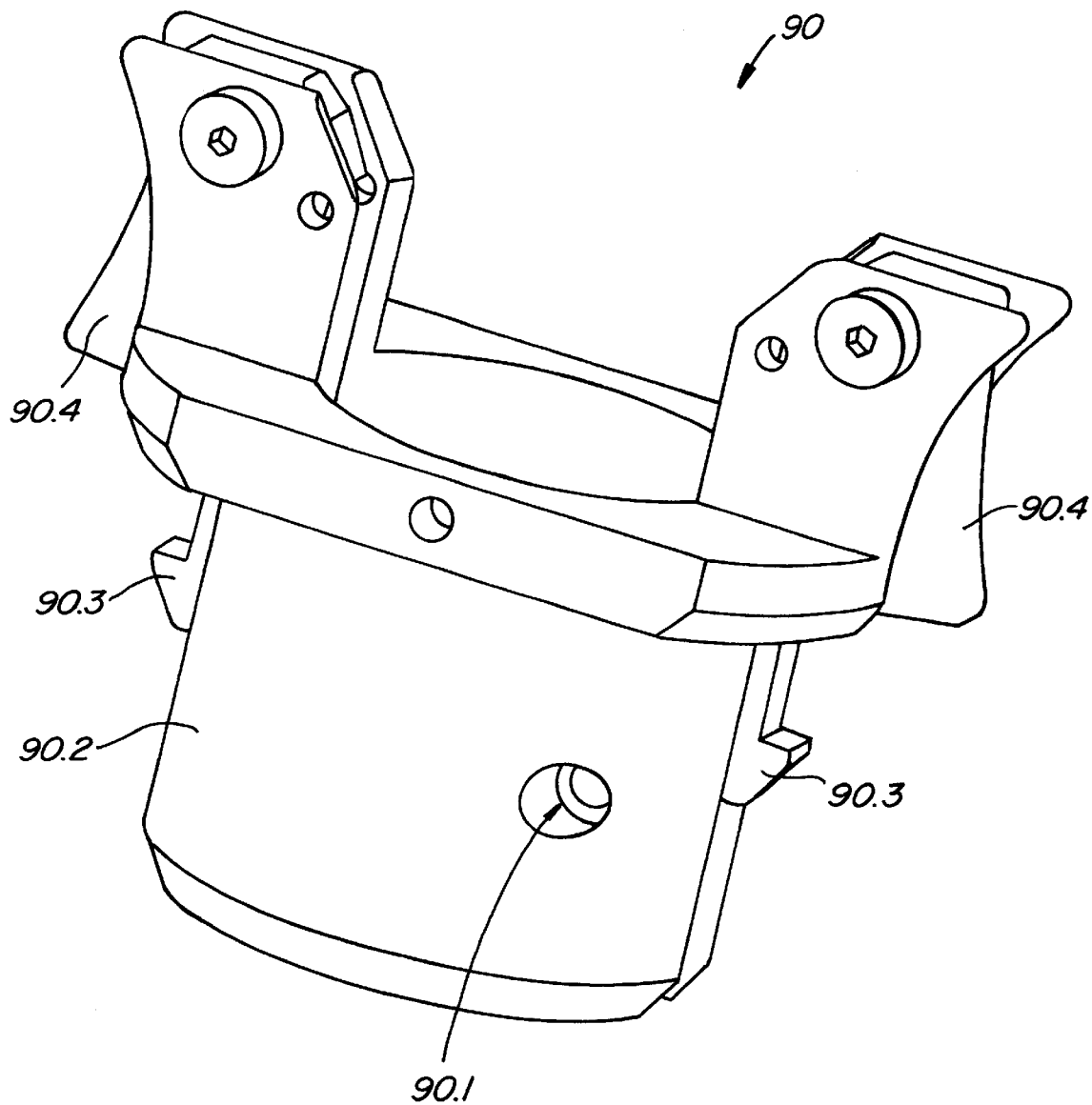
FIG. 10 shows a three-dimensional view of an endoscope locating formation.
Figure 11:
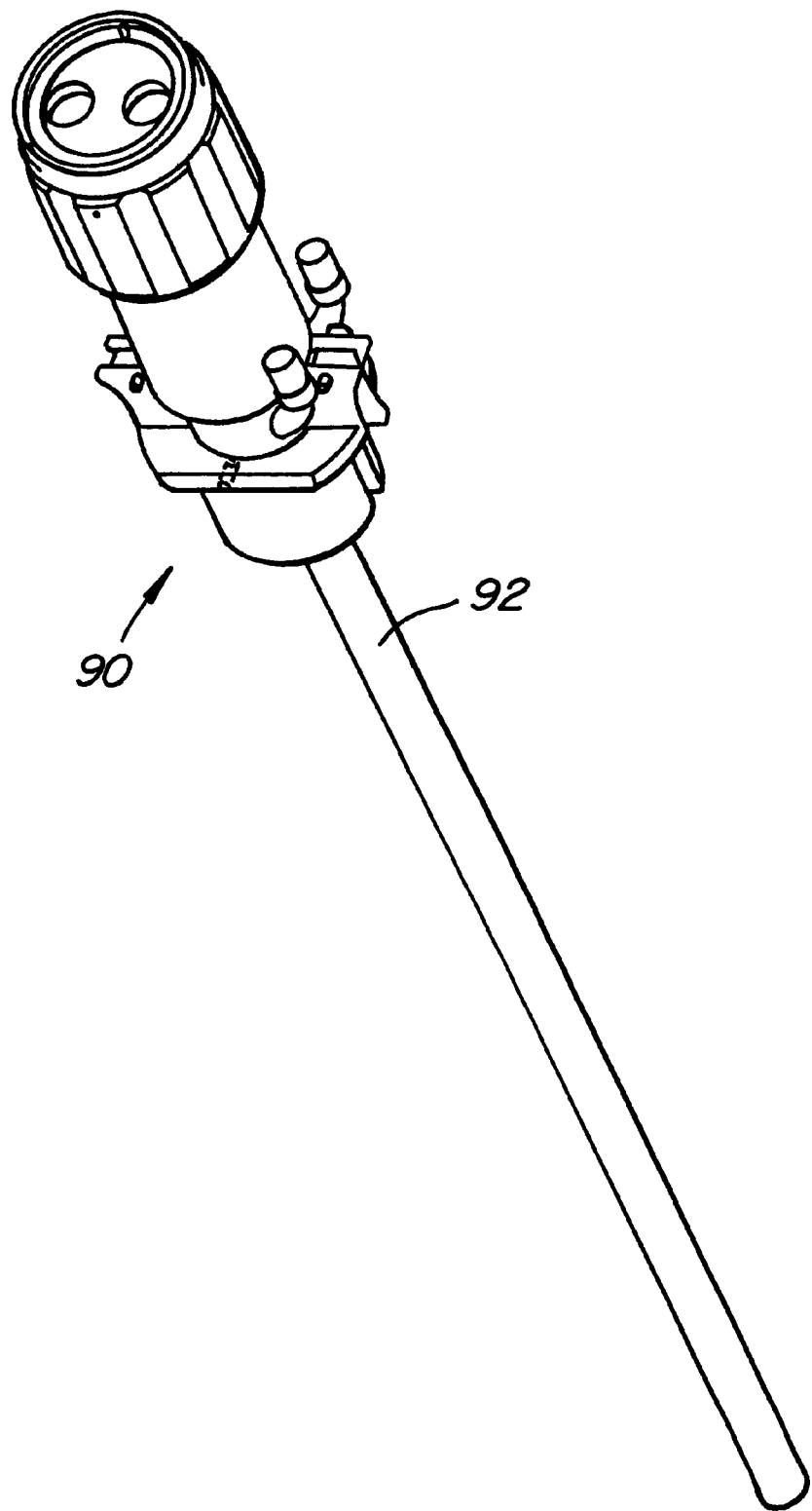
FIG. 11 shows, at a diminished scale, a three-dimensional view of the endoscope locating formation of FIG. 10 on an endoscope.
Figure 12:
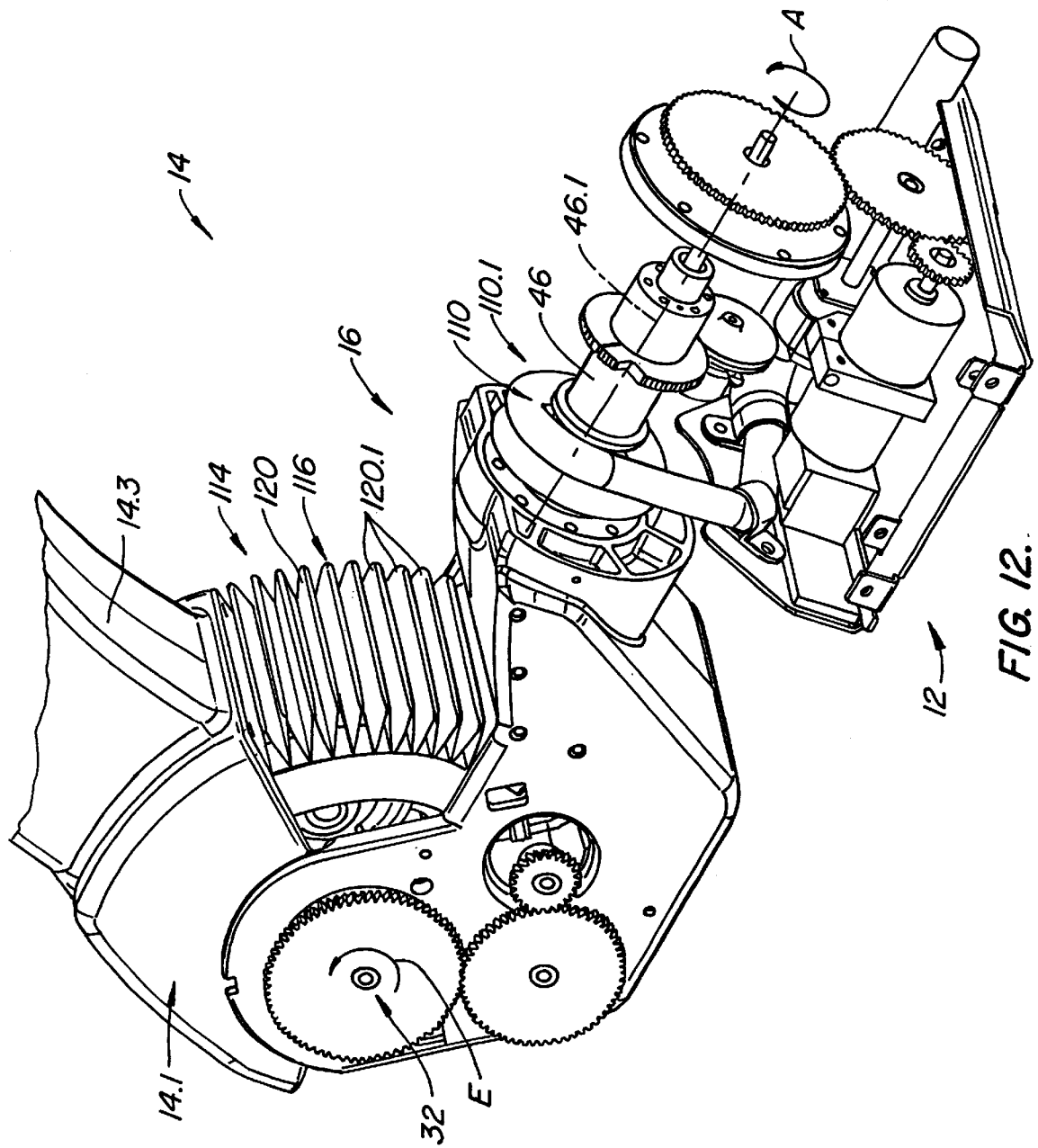
FIGS. 12 to 15 show, at an enlarged scale, three-dimensional views of a cradle portion of the arm shown in FIG. 1.
Figure 13:
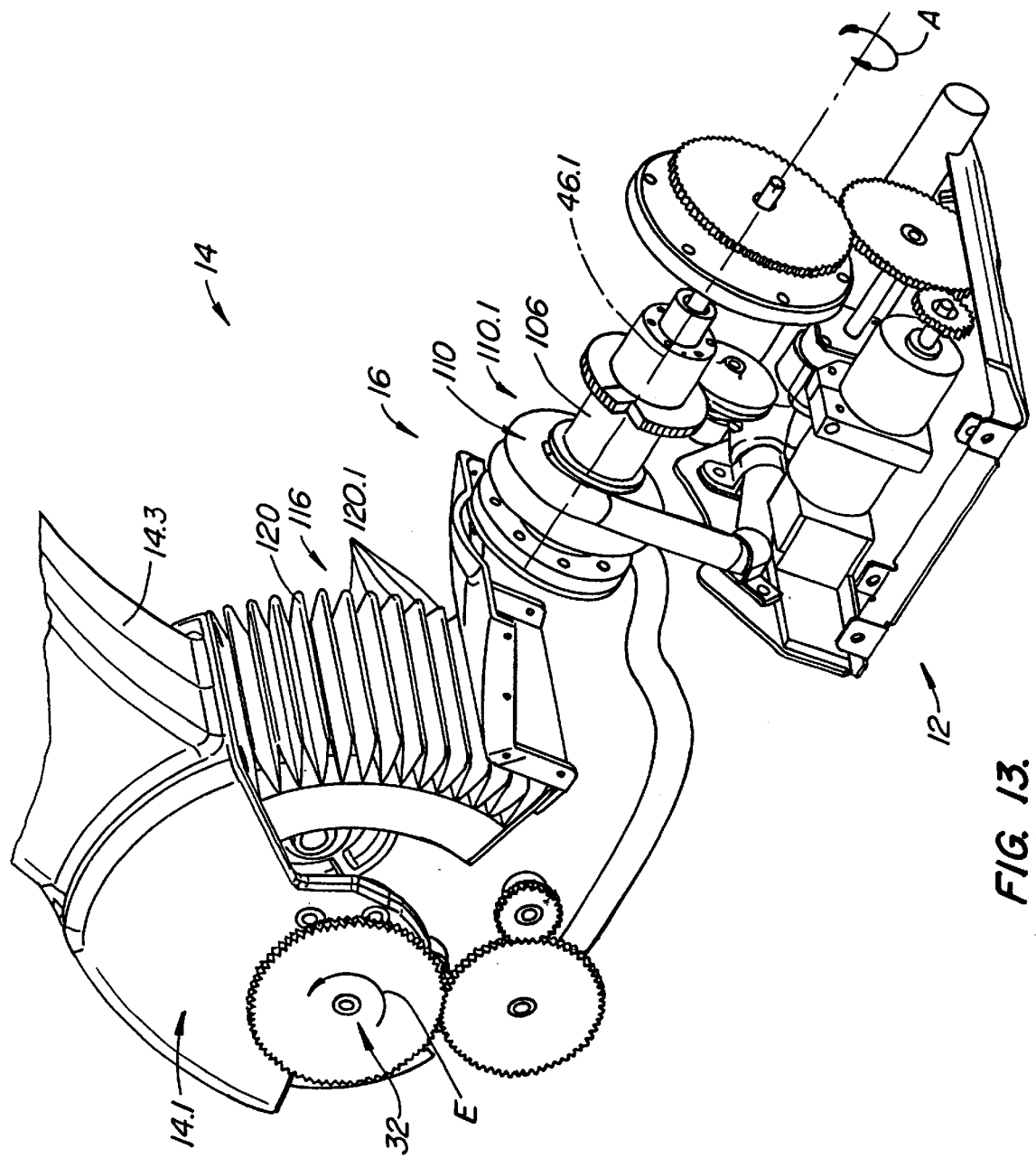
Figure 14:
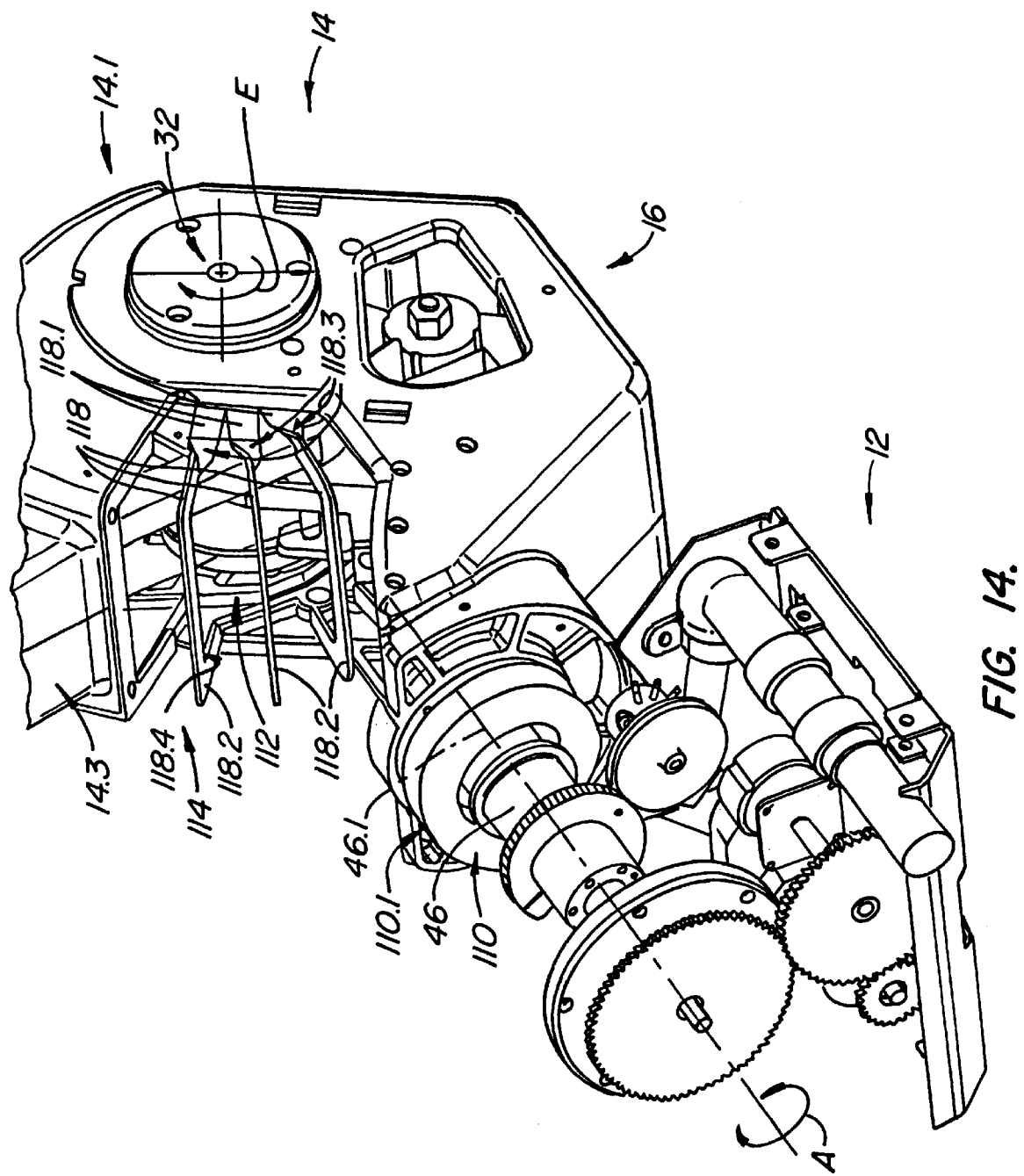
Figure 15:
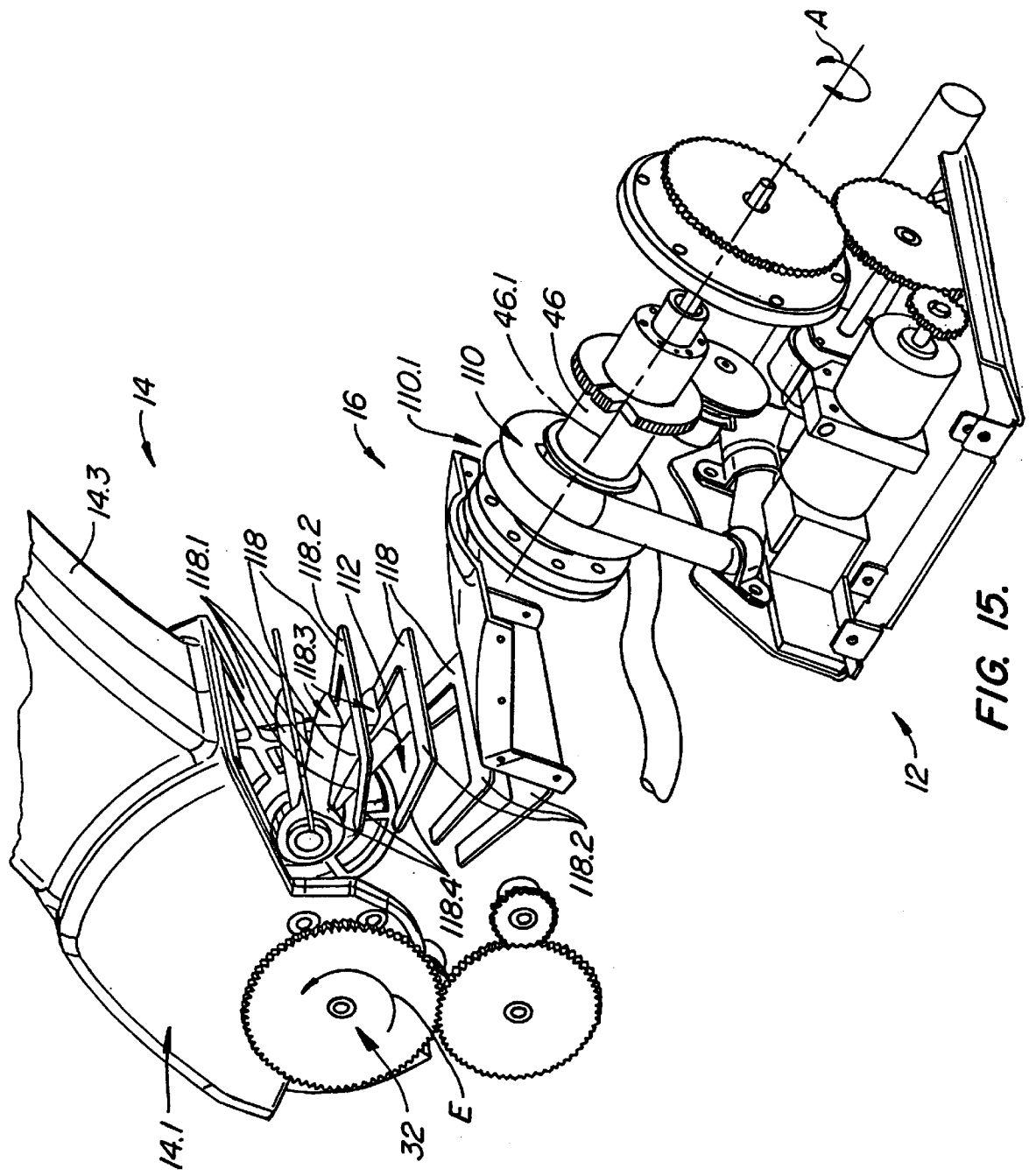

Referring now to FIGS. 9 to 11, the mounting of the endoscope will now be described in greater detail. With specific reference to FIG. 9, the collar 50 includes an axial aperture or passage 50.1. It further includes a part-circumferential outer surface 50.2. The surface 50.2 is complementary to a seat defined by a complementary internal surface 52.1 of the driven support 52, as can best be seen in FIG. 4. In use, the collar 50 is dropped into the driven support 52 male-female fashion, the surface 50.2 then facing the surface 52.1. The collar 50 has latches 50.3, only one of which is shown, the other being at a diametrically opposed position. Thus, when in a nested relationship with the support 52, the latches engage the support 52 releasably to lock the collar 50 on the support 52. The latches 50.3 are typically spring loaded. To this end, a leaf spring 50.4 is provided to urge the latches 50.3 into a locking attitude.

Referring now to FIG. 10, an endoscope locating formation is generally indicated by reference numeral 90. The formation 90 is typically releasably secured on an endoscope 92, as can best be seen in FIG. 11. Instead, the formation 90 can be permanently secured on the endoscope 92. The formation 90 is typically secured to the endoscope by sliding it into the position as shown in FIG. 11, and then securing it in place by means of a screw-threaded fastener at 90.1. The formation 90 has an outer circumferential extending surface 90.2. The surface 90.2 is complementary to an inner circumferential surface 50.5 of the collar 50 to permit the formation 90, when mounted on the endoscope 92, to be dropped into the passage 50.1 and into a nesting relationship with the surface 90.2 facing the surface 50.5.

The collar 50 has diametrically opposed axial slots 50.6. The formation 90 has diametrically opposed latches 90.3. When positioned on the collar 50, the latches 90.3 are guided along the slots 50.6 and releasably lock the formation 90 in position when in a fully nested position on the collar 50.

It will be seen that the collar 50 has a radially directed opening 50.7, which is complementary to a radially directed opening 52.7 of the support 52, as can be seen in FIG. 4. When mounted on the support 52, the opening 50.7 of the collar 50 is in register with the opening 52.7. When the endoscope locating formation 90 is secured on the endoscope, the endoscope 92 can be positioned in place by laterally passing a portion thereof through the registering openings 50.7, 52.7 and then dropping the endoscope so that the latches 90.3 are guided along the slots 50.6, until locked in position.

Buttons 90.4 are provided to cause disengagement of the latches 90.3 in response to pressing the buttons 90.4. The buttons 90.4 and latches 90.3 are arranged to permit quick engagement and disengagement of the formation 90 thereby to enable the endoscope to be mounted and dismounted on the arm relatively quickly. In use, it has been found that the endoscope may need to be periodically dismounted for cleaning purposes, or for replacement by a clean endoscope, during the course of a surgical procedure. By providing such relatively quick mountability and dismountability, the time between removing and replacing an endoscope is reduced.

Returning now to FIG. 4, the driven support 52 is driven to displace angularly by an appropriately positioned electrical motor (not shown), typically on the carriage 20, in operative communication therewith. The motor drives a gear 54 through an appropriate reduction gear train. The motor is typically a Maxon RE 013 motor with 16 pulse per revolution (PPR) magnetic encoder and has a 68:1 gear head ratio. The total reduction ratio between the motor and the driven support 52 is typically 300:1. The gear 54 has a shank portion 56. An elongate flexible element, e.g., a length of cable 57, is partially wound around the shank portion 56. Opposed end portions of the cable 57 extend from the shank portion 56 and over guide pulleys 58. Opposed ends 60, 62 of the cable 57 are secured to remote ends 52.1, 52.2 of the support 52 at 64 and 66 respectively, as can best be seen in FIG. 5. Accordingly, when the gear 54 is driven to displace angularly in the direction of arrows C, the support 52 is displaced in the directions of arrows D, as can best be seen in FIGS. 4 and 5. The support 52 is rollingly carried on the carriage 20 by means of suitably positioned ball bearings 68, as can best be seen in FIG. 5. The ball bearings 68 cooperate with a circumferentially extending track 70 defined along the outer circumference of the support 52.

Figure 6:
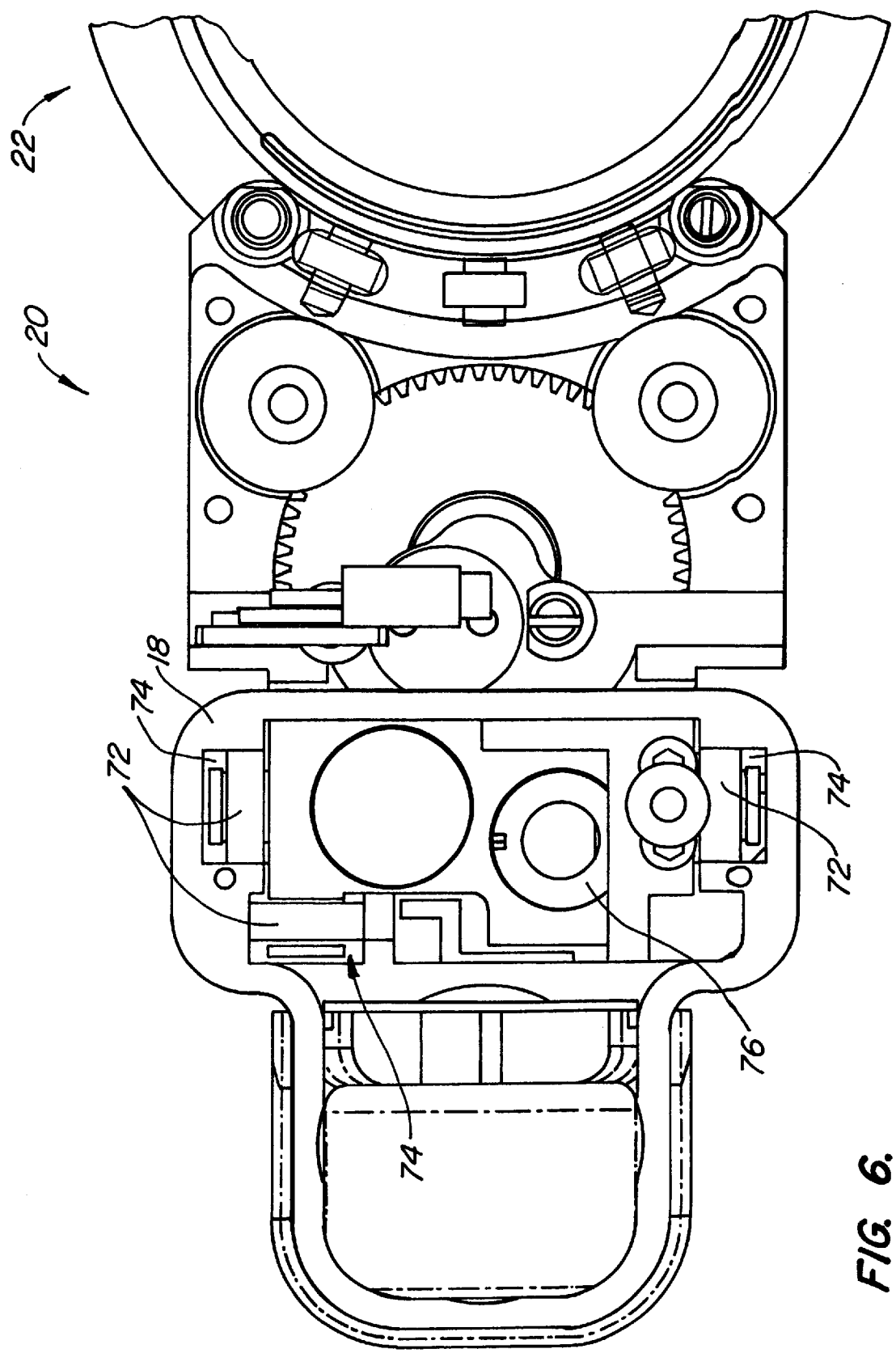
FIG. 6 shows a sectional view along arrows VI—VI in FIG. 2.

The carriage 20 can displace in opposed directions on the guide formation 18 as indicated by arrows B in FIGS. 1 to 3. The carriage 20 has ball bearings 72, as can best be seen in FIG. 6, which cooperate with longitudinally extending tracks 74 defined inside the guide formation 18. It will be appreciated that displacement of the carriage 20 along the tracks is accomplished by a suitably positioned electric motor (not shown) in operative communication with the carriage 20. The motor is typically a Maxon RE 025 motor with 160 PPR and HEDR encoder. The ratio between motor revolution and carriage displacement is typically 11.11 motor revolutions to 1 inch travel. The electric motor is typically secured on the guide formation 18 and its operative communication with the carriage 20 is typically established by means of a threaded shank or lead screw (not shown) mating with an internally threaded bush member or lead screw nut 76 on the carriage 20, as can best be seen in FIG. 6. It will be appreciated that the motor driving the carriage 20 and the motor driving the support 52 act through the master controls. The arrangement is such as to cause the carriage 20 to translate about ½ inch per revolution of the lead screw.

Figure 7:
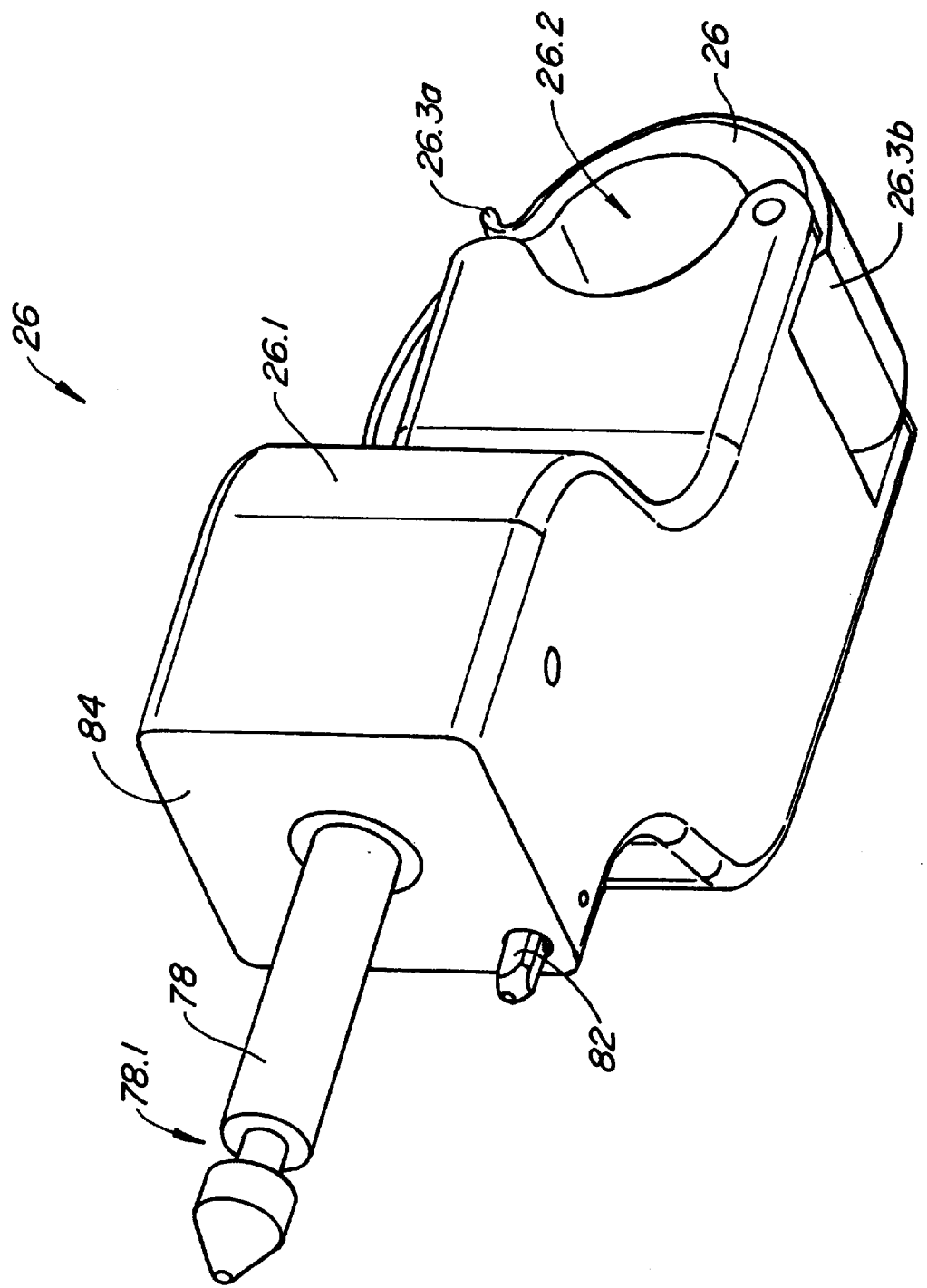
FIG. 7 shows a three-dimensional view of a cannula mount in an unmounted condition.
Figure 8:
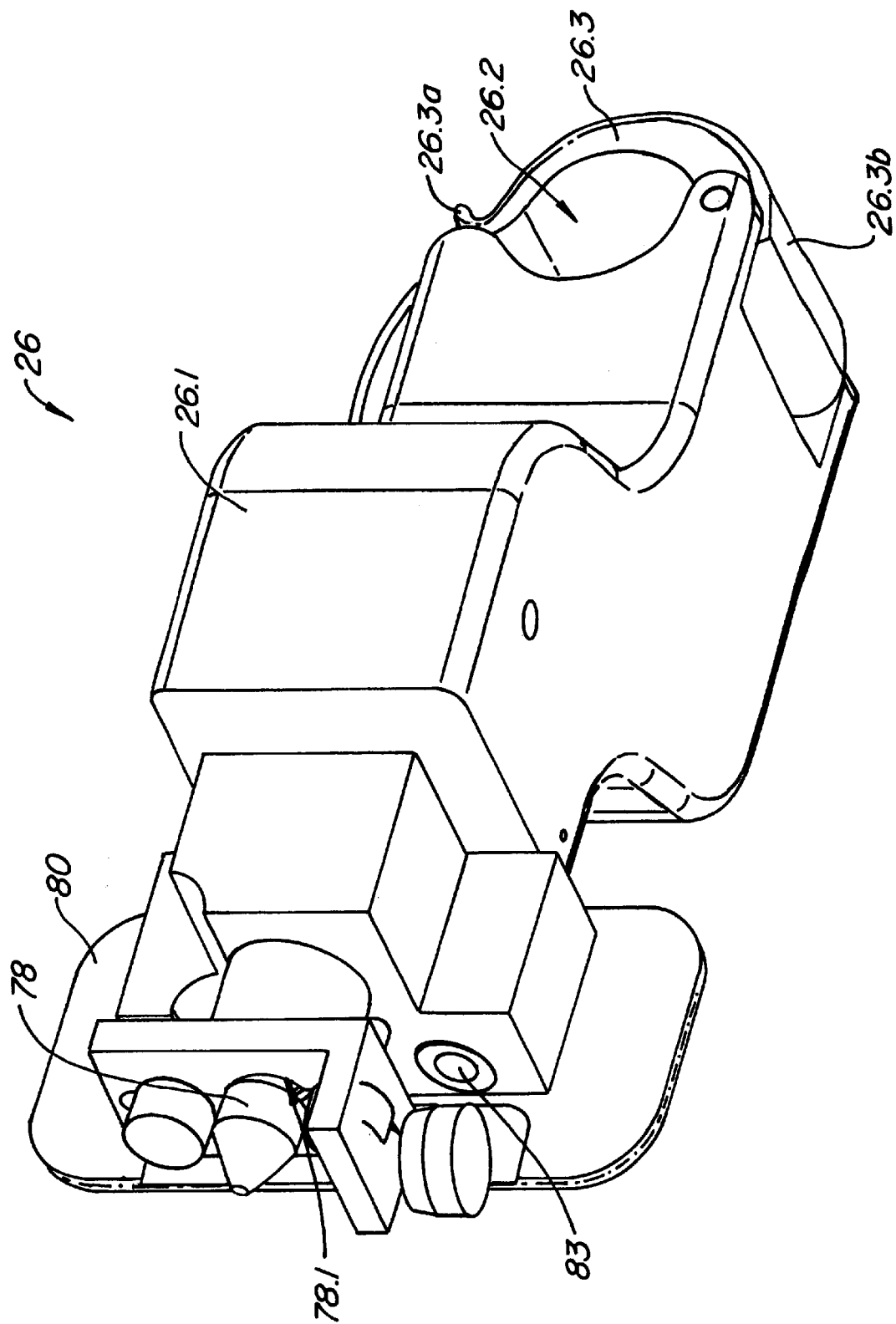
FIG. 8 shows a three-dimensional view of the cannula mount shown in FIG. 7, in a mounted condition on the arm.

Referring to FIGS. 7 and 8, the cannula mount 26 includes a body 26.1. The body 26.1 defines a mounting seat, generally indicated by reference numeral 26.2, in which the cannula is removably securable. The seat 26.2 is partly defined by the body 26.1 and partly by a bracket or gate 26.3. The bracket 26.3 has one end 26.3a, which is releasable securable to the body 26.2, typically by means of a spring loaded latch assembly on the body 26.1, and an opposed end 26.3b which is hingedly connected to the body 26.1. The bracket is arranged to clamp a cannula in the seat 26.2 when the bracket 26.3 is secured in a closed position, as indicated in FIGS. 7 and 8.

The bracket 26.3 and seat 26.2 arrangement is such as to ease the task of securing a cannula in the seat 26.2. The cannula is normally initially positioned relative to a surgical site. The mount 26, while mounted on the guide formation 18, is then brought to the cannula so as to be secure the cannula thereto. Thus, in use, the gate 26.3 is in an open position so that the cannula can be secured in the seat 26.2. Once in the seat 26.2, the gate 26.3 is closed and latched in its closed position.

The cannula mount 26 has an engagement pin 78 whereby it is releasably engageable with the guide formation 18. In FIG. 7, the cannula mount 26 is removed from the guide formation 18, and in FIG. 8, it is shown in an engaged position with a locking mechanism 80 secured on the guide formation. The locking mechanism 80 is typically spring loaded automatically to engage an annular groove 78.1 of the pin 78. To remove the cannula mount 26, a lever is activated to negate the working of the spring. The cannula mount 26 further includes a location stud or diamond pin 82 releasably locatable in a complimentary seat, or hole, 83 on the guide formation 26 to hold the cannula mount 26 in a specific position or orientation relative to the guide formation 18 when engaged therewith. It will be appreciated that, in use, the guide formation 18 is cloaked by means of a surgical drape so as to isolate it from a sterile surgical environment. When the cannula mount 26 is mounted on the guide formation 18, the engagement pin 78 and the locating stud 82 extend through the surgical drape, the surgical drape then being sandwiched between a face 84 of the cannula mount 26 and the guide formation 18. The cannula mount 26 is designed to be sterilizable so that it can be sterilized between surgical operations performed using the arm 14.

Further aspects of the arm 14 will now be described with reference to FIGS. 12 to 15 of the drawings, in which like reference numerals are used to designate similar parts unless otherwise stated. As mentioned, a plurality of actuators, e.g., electric motors, or the like, are mounted on the arm 14 to provide movement of the arm 14 within its four degrees of freedom of movement in response to actuation of the electric motors. One such electric motor is mounted on the carriage 20 to drive the endoscope mounting formation 22 to displace angularly relative to the carriage 20. Referring now to FIGS. 12 to 15, an electric harness, indicated at 110, extends from the base 12 to the arm 14 to provide electrical power to the electric motors on the arm 14. The harness 110 defines a spiral loop formation at 110.1. As mentioned, the cradle 16 can yaw relative to the base 12 as indicated by arrows A. The spiral loop 110.1 is arranged to enable the harness 110 to accommodate such yaw movement. As mentioned, the arm 14 has an electric motor mounted on the carriage 20. The harness 110 is operatively connected to the electric motor on the carriage 20. As can best be seen with reference to FIG. 1, the carriage 20 is arranged to translate in the direction of arrows B relative to the guide formation 18. The harness 110 has a rolling loop, not shown, arranged to accommodate the translation of the carriage 20 along the guide formation 18.

Still referring to FIGS. 12 to 15, and as already mentioned, the arm 14 is arranged to pitch about an axis 32 as indicated by arrows E. The cradle 16 comprises a plurality of working parts mounted within a chamber, as indicated by reference numeral 112 in FIGS. 14 and 15. The chamber 112 is defined within the cradle 16 and the part 14.1 of the arm 14. The cradle 16 and the part 14.1 define a mouth formation 114 which opens and closes in response to pitching of the arm 14 about the pivot 32. The arm 14 includes a bellows structure, generally indicated by reference numeral 116, to cover the mouth formation, so as, for example, to inhibit persons from being injured or pinched by the arm 14 at the mouth, when in use. The bellows formation 116 comprises a plurality of support members 118, as can best be seen with reference to FIGS. 14 and 15. Each support member 118 is generally in the form of a J-shaped member. The members 118 have elongate flat base portions 118.1. The base portions 118.1 have end portions (not shown) pivotally mounted on a shaft about which the arm portion 14.3 pivots relative to the cradle 16 at 32. The members 118 further define support fingers 118.2. The base portions 118.1 and the finger portions 118.2 are in the form of elongate flat, plate-like lengths. The flat lengths of the base portions 118.1 are arranged such that they are orientated generally to extend in a circumferential direction relative to the shaft at 32 and the flat lengths of the finger portions 118.2 are arranged such that they are orientated in a generally axial direction relative to the shaft at 32. Twist formations 118.3 link the finger portions 118.2 to the base portions 118.1.

The bellows formation 114 further includes a bellows body 120, typically of a synthetic plastics material, e.g., rubber, or the like, arranged to collapse and extend in sympathy with pitching of the arm 14 about the pivot 32. The bellows body 120 has a plurality of collapsible pleat formations 120.1. The finger portions 118.2 seat in some of the pleat formations 120.1, for example, every second or third pleat formation, to support the bellows body 120.

Each support member 118 has a distal radially inwardly directed end portion 118.4 connected to a distal end of each finger 118.2. Although the portions 118.4 are typically not connected to the shaft at 32, due to, for example, gears and drive trains being positioned in the chamber 112 to render connection of the portions 118.4 to the shaft at 32 cumbersome, the portions allow the bellows body 120 to retract, or collapse, relatively evenly, when compared with members similar to the members 118, but without such end portions or extensions.

The twist formations 118.3 direct the finger portions 118.2 to extend generally parallel with, or axially relative to, the shaft at 32. The portions 118.1 extend radially from the shaft at 32. The configuration of the plate-like portions of the portions 118.1 is such as to permit them to be stacked against each other on the shaft while taking up relatively little space in an axial direction. Similarly, the configuration of the platelike portions of the fingers 118.2 is such as to permit them to be stacked relatively closely adjacent each other thereby to enable the bellows body 120 to collapse into a relatively compact configuration.

Referring to FIG. 16, in this embodiment, an endoscope 22 is supported by an articulated arm 14 having an endoscope between two tissue manipulation tools 119. One or more of the robotic arms will often support a surgical tool which may be articulated (such as jaws, scissors, graspers, needle holders, microdissectors, staple appliers, tackers, suction/irrigation tools, clip appliers, or the like) or non-articulated (such as cutting blades, cautery probes, irrigators, catheters, suction orifices, or the like). The end effector tool 120 has four degrees of freedom relative to a support bracket of manipulator 119. Motors are coupled to tool 120, which is coupled to mounting formation 121, so as to rotate the tool about an axis, and often to articulate a wrist at the distal end of the tool about at least one, and often two, degrees of freedom. One or more of the robotic arms will often be used to support one or more surgical image capture devices such as an endoscope (which may be any of the variety of structures such as a laparoscope, an arthroscope, a hysteroscope, or the like), or optionally, some other imaging modality (such as ultrasound, fluoroscopy, magnetic resonance imaging, or the like). Typically, the robotic arms 119 will support at least two surgical tools corresponding to the two hands of a surgeon and one optical image capture device.

Although the present invention is disclosed in the context of supporting an endoscope or other image capture device, it will be apparent that this type of construction for a robotic arm might also be successfully used to support any other type of robotic surgical instrument, such as the types disclosed in co-pending U.S. patent application Ser. Nos. 09/398,958, entitled "Surgical Tools for Use in Minimally Invasive Telesurgical Applications," filed Sep. 17, 1999, and 09/418,726, entitled "Surgical Robotic Tools, Data Architecture, and Use," filed Oct. 15, 1999, the entireties of which are herein incorporated by reference.

While the above is a complete description of preferred embodiments of the invention, various alternatives, modifications and equivalents may be used. It should be evident that the present invention is equally applicable by making appropriate modifications to the embodiments described above. Therefore, the above description should not be taken as limiting the scope of the invention which is defined by the metes and bounds of the appended claims along with their full scope of equivalents.

What is claimed is:

1. A positional control system for varying the position of at least one robotic surgical tool, the positional control system including: a base, a first articulated arm having a first end mounted on the base and an opposed second end arranged to be positionally adjustable relative to the base, the first articulated arm having an upper arm portion, a forearm portion, a forearm link member and an upper arm link member; a first mounting formation on the second end of the first articulated arm and arranged to support a first robotic surgical tool, wherein the upper arm portion, the forearm link portion, the forearm link member, and the upper arm link members of the first articulated arm are pivotally secured to each other to effect displacement of the first mounting formation relative to the base; the forearm link member is positioned at least partially within the forearm portion and the upper arm link member is positioned at least partially within the upper arm portion; at least one actuator for driving the first articulated arm to cause positional adjustment of the second end relative to the base; a drive system comprising at least one harmonic drive operatively positioned between the actuator and the first articulated arm so as to articulate the first articulated arm, the drive system being backdrivable so that movement of the first robotic surgical tool effects movement of the actuator.

2. The positional control system of claim 1, further comprising the first robotic surgical tool, wherein the first robotic surgical tool comprises an image capture device.

3. The positional control system of claim 2, further comprising a second robotic surgical tool and a second articulated arm having a first end mounted on the base and a second mounting formation on an opposed second end arranged to support a second robotic surgical tool, wherein the second robotic surgical tool comprises a tissue manipulating surgical end effector.

4. The positional control system of claim 3, further comprising a third robotic surgical tool and a third articulated arm having a first end mounted on the base and a third mounting formation on an opposed second end arranged to support a third robotic surgical tool, wherein the third robotic surgical tool comprises a second tissue manipulating surgical end effector.

5. The positional control system of claim 1, wherein the first articulated arm is supported entirely by an single cantilevered, pivotal connection between said upper arm portion and said base.

6. The positional control system of claim 1, wherein the harmonic drive has a drive gear ratio, and wherein the drive system further comprises a gear train coupled to the harmonic drive so as to generate a drive system gear ratio, the drive system gear ratio being a larger multiple of the harmonic drive gear ratio.

7. The positional control system of claim 1, wherein the first articulated arm further comprises a brake.

8. The positional control system of claim 7, wherein the brake auto locks at least one joint of the first articulated arm.

* * * * *